United States Patent [19]

Akiba et al.

[11] 4,342,515
[45] Aug. 3, 1982

[54] METHOD OF INSPECTING THE SURFACE OF AN OBJECT AND APPARATUS THEREFOR

[75] Inventors: Masakuni Akiba, Tokorozawa; Hiroto Nagatomo, Tokyo; Jun Suzuki, Higashimurayama, all of Japan

[73] Assignee: Hitachi, Ltd., Tokyo, Japan

[21] Appl. No.: 5,924

[22] Filed: Jan. 23, 1979

[30] Foreign Application Priority Data

Jan. 27, 1978 [JP] Japan .................................. 53-7277
Jan. 12, 1979 [JP] Japan .................................. 54-1356

[51] Int. Cl.³ .......................................... G01M 21/32
[52] U.S. Cl. .................... 356/237; 356/239; 356/369
[58] Field of Search ................... 356/237, 369, 239

[56] References Cited

U.S. PATENT DOCUMENTS

2,947,212 8/1960 Woods .............................. 356/369
3,972,619 8/1976 Stevens ........................... 356/369
4,020,695 5/1977 Roney .............................. 356/369

*Primary Examiner*—Harold A. Dixon
*Attorney, Agent, or Firm*—Craig and Antonelli

[57] ABSTRACT

This invention discloses inspection apparatus for detecting unfavorable foreign matters existent on the surface of an object such as semiconductor wafer. The apparatus includes a collimated beam generator portion which projects a collimated beam towards the object to-be-inspected from a side thereof, and a mechanism which senses light reflected from the surface of the object, through a polarizer plate. In accordance with this invention, the signal-to-noise ratio between a detection signal generated by a pattern of the foreign matter to-be-detected and a signal generated by a normal pattern of the object surface and sensed as a noise component can be enhanced.

6 Claims, 14 Drawing Figures

METHOD OF INSPECTING THE SURFACE OF AN OBJECT AND APPARATUS THEREFOR

BACKGROUND OF THE INVENTION

This invention relates to a method of inspecting the surface of an object for detecting unfavorable foreign matter existent on a surface, and apparatus therefor. More particularly, it relates to a method of detecting foreign matter suitable for the inspection of the external appearance of a surface of a semiconductor wafer, and apparatus therefor.

In the manufacturing steps of a semiconductor device such as formation of a passivation film and formation of a metallic interconnection, foreign matter of an insulating substance, a metallic substance, dust etc. often adheres to undesired areas of the surface of a semiconductor wafer. The foreign matter forms a cause for noticeably lowering the yield or available percentage of the semiconductor device. In the process management, therefore, it is necessary to determine the sizes, number etc. of the foreign matter in advance. Accordingly, an inspection on the foreign matters on the semiconductor wafer is required between the actual manufacturing steps of the semiconductor device.

Heretofore, the inspection on the foreign matter has been usually made by the visual inspection employing a metallurgical microscope (of, for example, 100–200 magnifications). This method has the problem that the inspector's subjectivity is prone to be involved in the judgement of a foreign matter, so the inspected results differ depending upon inspectors, and the problem that a long time is taken for the inspection (2–3 hours for one semiconductor wafer). It is therefore impossible to accurately and promptly offer the result of the interstep inspection and to perform an appropriate process management, so that the lowering of the yield cannot be effected.

Although not relevant to the foreign matter detecting method taken up as the subject of this invention, a method of inspecting the evaporated state of a metal film in a semiconductor device has been proposed in Japanese patent application Publication No. 32539/1976. According to the method, the surface of the semiconductor device is illuminated by a collimated beam, and by exploiting the difference of the directivities of irregularly reflected light from the metal film and irregularly reflected light from an insulating film of the semiconductor device on which the metal film ought to be evaporated, the irregularly reflected light from the evaporated metallic pattern is converted into an electric signal, whereby the metallic pattern is judged to be conformable or defective. Such a method of inspecting the pattern of the metal film is, in the end, achieved for the first time when the different substances of the insulating film such as silicon oxide film and the metal film to be evaporated thereon are combined. In case of intending to apply such a method to the automation of foreign matter detection, problems to be described below are posed. The semiconductor device to be inspected includes, for example, a protuberance of a normal pattern which has been formed by a metallic interconnection layer and an unfavorable protuberance of a foreign matter which has developed due to the step of evaporating a metal. Therefore, when the surface of the semiconductor device is illuminated by the collimated beam and the reflected light is converted into the electric signal, the detected electric signal of the protuberance of the normal pattern becomes a noise component to the detected electric signal of the protuberance of the foreign matter. This results in the difficulty of the discrimination between foreign matter and the normal pattern. Moreover, in the case where a foreign matter has been formed on a substrate made of the same substance as that of the foreign matter, for example, where the normal pattern of a passivation film of phosphosilicate glass formed by the chemical vapor deposition (CVD) process has been overlain by foreign matter of the phosphosilicate glass appearing during the process, the optical properties of the foreign matter and the normal pattern are identical, so that the discrimination of the foreign matter is very difficult.

SUMMARY OF THE INVENTION

It is accordingly the principal object of this invention to provide a method of inspection capable of readily detecting foreign matter and apparatus therefor.

Another object of this invention is to provide a method of inspection capable of detecting even foreign matter of the same substance as that forming a normal pattern and apparatus therefor.

Still another object of this invention is to enhance the signal-to-noise ratio in an inspection on foreign matter in which the detected result of the foreign matter is converted into an electric signal.

The above-mentioned and other objects, features and advantages of this invention will be fully understood from the following description of embodiments taken with reference to the drawings.

DESCRIPTION OF THE PREFERRED EMBODIMENTS

Figure 1:
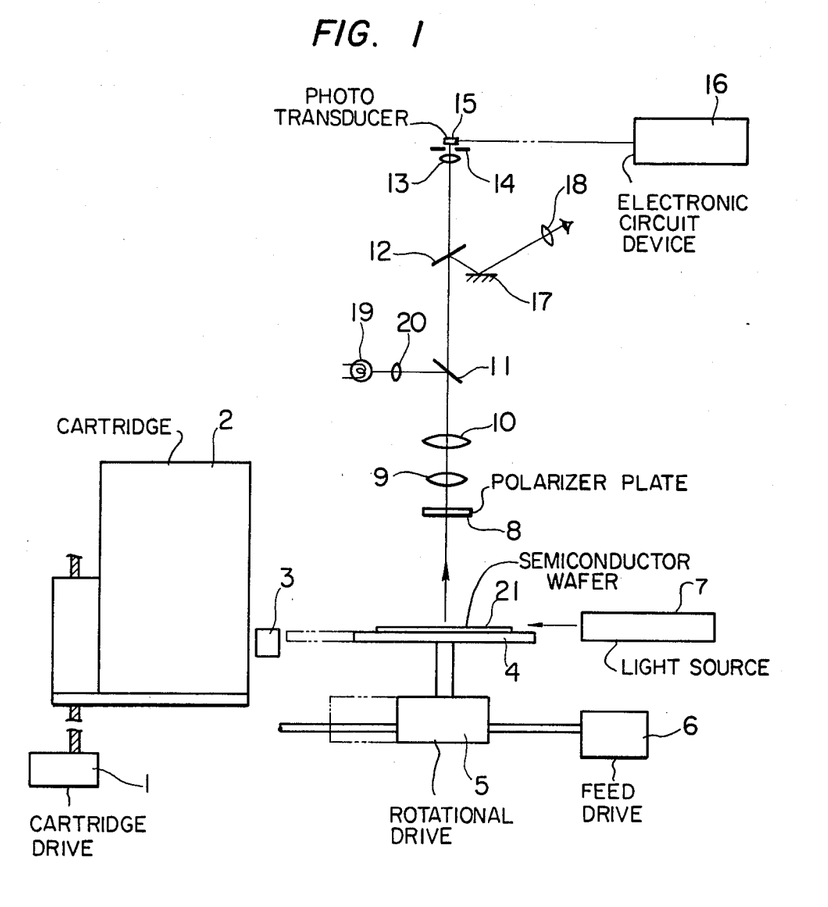
FIG. 1 is a schematic arrangement view showing foreign matter detection apparatus according to an embodiment of this invention.

FIG. 1 is a constructional view which shows foreign matter detection apparatus according to an embodiment of this invention.

Numeral 1 designates a cartridge feed drive portion which moves in the vertical direction a cartridge 2 for accommodating semiconductor wafers. Numeral 3 designates a wafer feed portion which transfers the semiconductor wafer between the cartridge 2 and a wafer rest 4. A rotational drive mechanism portion 5 serves to rotate the semiconductor wafer rest 4, while a feed drive portion 6 serves to move the rest 4 in the horizontal direction.

Shown at 7 is a light source for generating a collimated beam. Numeral 8 indicates a polarizer plate which is constructed of two transparent glass plates having inclined planes and by sticking the inclined planes with each other, and which has the function of acting on light from the semiconductor wafer rest 4 to intercept light waves in a predetermined amplitude direction. The polarizer plate may also be Nicol's prism or any other polarizing prism, an artificial polarizer plate, a glass plate slanted appropriately, or the like. Numerals 9 and 10 indicate objectives. Numeral 11 indicates a mirror for projecting illumination light for visual inspection, numeral 12 a mirror for the visual inspection, numeral 13 a relay lens, and numeral 14 an aperture plate. A photoelectric transducer 15 converts light into an electric signal, and an electronic circuit device 16 processes the output information of the photoelectric transducer to provide an inspected result. Numeral 17 represents a mirror for the visual observation adapted to reflect light towards an ocular lens 18, numeral 19 a lamp for emitting the illumination light for the visual observation, numeral 20 a condensing lens, and numeral 21 the semiconductor wafer to-be-inspected. The mirrors 11, 12 and 17, the lenses 18 and 20 and the lamp 19 are components for realizing the visual inspection, and are not indispensable.

The inspection with the foreign matter detection apparatus is conducted as follows.

The semiconductor wafer in the cartridge 2 is transferred onto the rest 4, and fixed to the central part of the rest 4. Under this state, the laser beam is projected sidewards of the semiconductor wafer 21 and in parallel with the surface of the wafer. While rotating the rest 4, the reflected light from the semiconductor wafer 21 is detected through the photoelectric transducer 15, and the polarizer plate 8 is set at an angle of rotation at which the polarized light is cut by the polarizer plate 8 and at which only the unpolarized light can be detected. The sizes and number of foreign matter are detected on the basis of the reflected light in this state. Since the detection of the reflected light is done by magnifying the wafer surface by means of the lenses 9, 10 and 13 (to, for example, 20 diameters), the field of view is narrow. Therefore, a part to be detected is moved relative to the optical detection system including the lenses etc. by moving the rest 4 (with the drive portions 5 and 6), whereby the semiconductor wafer is inspected over the whole surface. Upon completion of the inspection of one semiconductor wafer, this semiconductor wafer is returned to the cartridge 2, and the inspection is made on the next semiconductor wafer.

The light of the light source 7 need not always be the laser light. The light may well be the natural light. In case of using the laser light beam, the wavelength and the phase change regularly and the illumination energy therefore becomes high, so that a high detection sensitivity can be attained.

This invention exploits the property of the wave directivity of light, and achieves its purpose owing to the combination of this property and the polarizer plate. The principle of this invention is considered as below.

Strictly, the amplitude of light is to be expressed as a vector quantity, not as a scalar quantity, and it has not only a magnitude but also a directivity. Light is a kind of electromagnetic wave, and as revealed by Maxwell's theory, it has the property that the wave of an electric field and the wave of a magnetic field travel while oscillating within a plane orthogonal to the propagating direction of the light and that the directions of their vectors are orthogonal to each other. Accordingly, at least light which is not polarized at all, i.e. the natural light as emitted from the light source can be divided into the components of a vertical wave indicated by a solid line 22 in FIG. 2 and a horizontal wave indicated by a broken line 23 in the figure. (Since the horizontal wave has an amplitude perpendicular to the drawing, it cannot be actually depicted in the figure. For convenience's sake, however, it is shown likewise to the vertical wave.)

Figure 2:
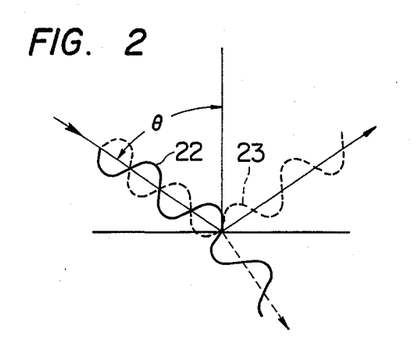
FIG. 2 is a diagram for explaining that the vertical component of light projected on an object at angles of incidence within a certain extent is refracted, whereas the horizontal component is reflected.

As illustrated in FIG. 2, the natural light projected onto the interface between media of unequal refractive indices can undergo the polarized reflection phenomenon in which most of the vertical wave is refracted and most of the horizontal wave is reflected, because the angle of incidence on the interface differs between the vertical wave and the horizontal wave. This phenomenon is a manifestation of Brewster's law that the quantity of polarization of reflected light from an object varies depending upon the angle of incidence and that it becomes the maximum when the angle of incidence is the polarization angle of the object. That is, the proportion in which the reflected light is polarized into the two light waves of the horizontal wave and the vertical wave differs in dependence on the angle of incidence. When the angle of incidence is the polarization angle, the perfect plane polarization (horizontal wave) is given forth.

This invention has been made with note taken of such a polarization phenomenon. It is deemed to utilize the fact that the quantity of polarization of reflected light from the surface of a normal pattern and the quantity of polarization of reflected light from the surface of unfavorable foreign matter in a semiconductor wafer to-be-inspected are unequal.

Figure 3:
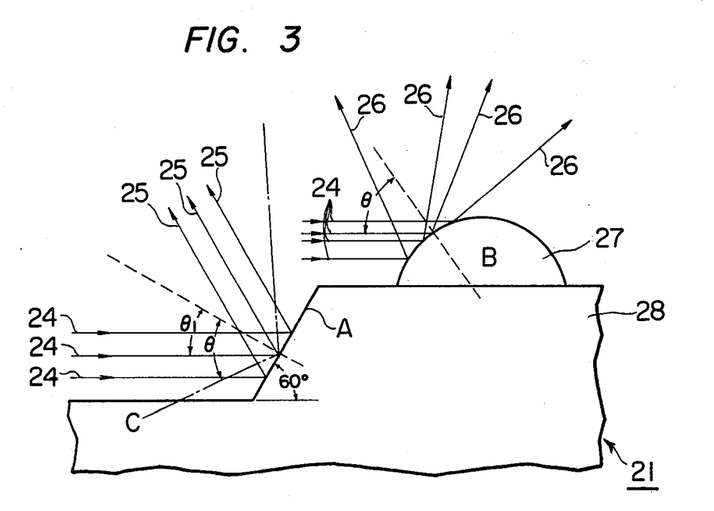
FIG. 3 is a diagram for explaining the difference between reflected light from an etched face and reflected light from foreign matter in the surface of a semiconductor wafer to-be-inspected.

Referring to FIG. 3, the semiconductor wafer 21 to be inspected is shown in a partially enlarged view. Light 24 is projected sidewards of the semiconductor wafer 21 under the state of a collimated beam (for example, laser beam). A passivation film 28 made of phosphosilicate glass has formed a normal pattern, and an etched face of the pattern is denoted by A. At the formation of the passivation film 28, a foreign matter 27 of the glass has adhered on the film, and the surface of the foreign matter is denoted by B. The stand face A of the normal pattern has a reflective surface which is slanted in a certain fixed direction, whereas the surface B of the foreign matter 27 has rough surface areas which are slanted in all directions.

Assuming that the face A of the glass passivation film 28 has been formed at an inclination of about 60° by etching, the angle of incidence of the light 24 on the etched face in this case is about 30° ($\theta_1$). In contrast, the angle of incidence on the surface B of the foreign matter 5 varies from 0° to 90° and is not fixed.

Under such a state, the polarization angle of the glass passivation film 28 is approximately 55° ($\theta$), and the polarization angle at the surface of the foreign matter 27 is also approximately 55° ($\theta$).

Accordingly, light 25 reflected from the etched face A of the passivation film 28 is polarized 80% because the angle of incidence is comparatively close to the polarization angle. On the other hand, regarding light 26 reflected from the foreign matter surface B, 80% of the light rays reflected from only the surface areas having the angle of incidence of 55° ($\theta$) are polarized, and all the other light rays forming the greater portion of the total reflected light are not polarized. That is, the light reflected from the etched face has its greater portion (80% in the above example) polarized and exhibits a fixed directivity, whereas the light reflected from the surface of the foreign matter has only an extremely small portion polarized and has not the greater portion polarized and it does not exhibit a fixed directivity.

Accordingly, when the surface of the semiconductor wafer is observed through the polarizer plate 8 (not shown in FIG. 3), only the unpolarized light is seen, and the state in which the polarized light is cut can be established. In other words, the state in which only the unpolarized light reflected from the foreign matter is sensed and any other thing is not seen at all (or any other thing is negligible on account of very feeble light) is established. All the sensed light in this state comes from the foreign matter. Therefore, the foreign matter detection can be automatically effected in such a way that an electric signal obtained by the photoelectric conversion of the sensed light is processed in the electronic circuit device.

The principle of this invention can also be explained as follows.

The angle of the inclined face A of the etched part in the semiconductor wafer 21 is 60°. The collimated light beam projected has most of its vertical wave refracted and absorbed into the semiconductor wafer, whereas its horizontal wave is reflected. Since the etched face A can be said, in effect, to be a mirror surface (plane), the reflection is the mirror surface (plane) reflection, and the directions of the reflected light rays are almost equal.

On the other hand, since the surface of the foreign matter is of course a non-mirror surface (curved surface), the light projected on the foreign matter has dispersed values of angles of incidence. Therefore, it is not the case that only the horizontal wave is reflected, but both the horizontal wave and the vertical wave are reflected (of course, part of the horizontal wave and part of the vertical wave are refracted and absorbed into the semiconductor wafer).

That is, all the light rays reflected from the etched face have the fixed directivity, whereas the light rays reflected from the foreign matter are irregularly reflected in separate directions and do not have any fixed directivity.

Therefore, the light reflected from the etched face can be cut by the polarizer plate 8 so as to sense only the irregular reflection light of the foreign matter.

The rotation of the polarizer plate 8 in the inspection is effected in order that the angle of the light to be cut by the polarizer plate 8 may be fitted to the direction of the light actually reflected from the etched face.

The principle of this invention can further be explained as follows.

The laser light for use in the inspection is originally light in a fixed direction. Since it is reflected without any change from an inclined surface of fixed angle, only the horizontal wave is obtained as illustrated in FIG. 2. On the other hand, the foreign matter has innumerable minute inclined surface areas of various angles, so that the reflected light of the vertical wave is also obtained from the surface of the foreign matter. Therefore, even when the polarizer plate is interposed, the light from the foreign matter is sensed. Conversely stated, the presence of the foreign matter can be confirmed owing to the sensed light.

Figure 4A:
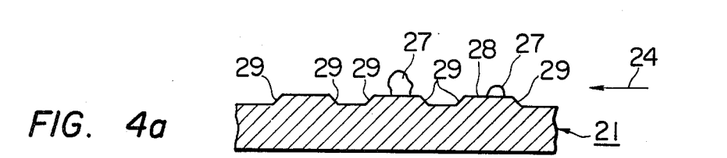
FIGS. 4a to 4e are views for explaining the process in which foreign matter on the surface of a semiconductor wafer is converted into electric signals.
Figures 4B, 4C:
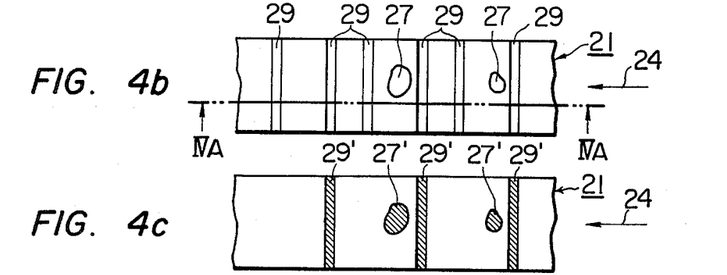
Figure 4D:
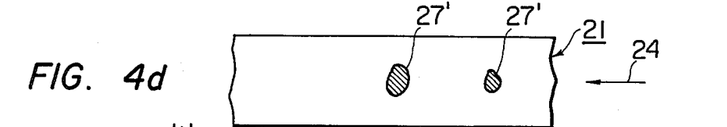
Figure 4E:
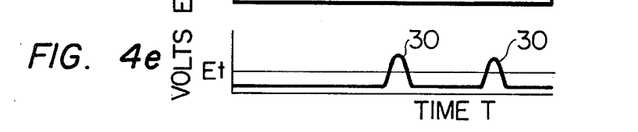

FIG. 4e shows an example of an electric signal waveform which has been provided by the electronic circuit device 16 electrically coupled with the photoelectric transducer 15 shown in FIG. 1. It is supposed that, as shown in FIGS. 4a and 4b, the semiconductor wafer 21 to be inspected includes bumps 28 formed according to a normal pattern, each bump having walls 29 which define both end parts thereof. It is also supposed that unfavorable foreign matter 27 adheres on two of the bumps 28. Such a semiconductor wafer 21 is set on the foreign matter detection apparatus of this invention as shown in FIG. 1, and light 24 is projected from the right-hand side in respective figures as illustrated in FIGS. 4a–4e. If the polarizer plate 8 (FIG. 1) is situated at a position at which it does not cut the light wave in a specified direction (for example, horizontal wave) of the reflected light from the semiconductor wafer 21, a glistening pattern which can be observed at the position of the photoelectric transducer 15 will consist of foreign matter areas 27' corresponding to the shapes of the foreign matter 27 and wall areas 29' corresponding to the shape of the walls 29 illuminated from the righthand side as illustrated in FIG. 4c. In this case, the polarizer plate 8 is located so as to pass the reflected light of both the foreign matter 27 and the walls 29, and hence, the foreign matter pattern areas 27' and the normal pattern areas 29' cannot be distinguished.

By rotating for adjustment the polarizer plate 8 clockwise or counterclockwise within a certain horizontal plane parallel to the rest 4 and about the path of the light of the optical system of the apparatus shown in FIG. 1, the light reflected from the walls 29 having the normal pattern can be cut by the polarizer plate 8, and only the light reflected from the foreign matter 27 can be passed therethrough. This is considered to be based on the principles stated previously. As a result, the observation pattern shown in FIG. 4c can be brought into an observation pattern shown in FIG. 4d. As illustrated in FIG. 4d, only the foreign matter pattern areas 27' corresponding to the foreign matters 27 can be observed as if they were sprinkling stars.

The electronic circuit device 16 compares electric signals 30 provided in correspondence with the foreign matter pattern areas by the photoelectric transducer 15, with a threshold voltage $E_t$ as illustrated in FIG. 4e, and forms pulse signals corresponding to the foreign matter pattern areas.

Figure 5:
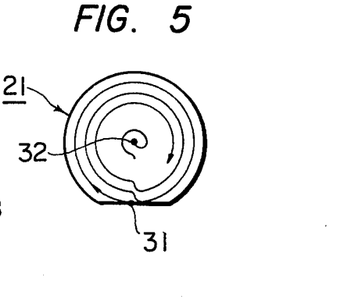
FIG. 5 is a view for explaining a method of detecting foreign matters over the whole surface of a semiconductor wafer.

As illustrated by way of example in FIG. 5, in case of detecting foreign matters of a circular semiconductor wafer 21, the semiconductor wafer 21 is placed on the rest 4 shown in FIG. 1, and the light from the light source 7 is concentrically scanned from the outer peripheral part 31 of the wafer 21 towards the center thereof by rotating the semiconductor wafer 21 by means of the rotational drive mechanism portion 5, whereby the states of various parts of the semiconductor wafer surface can be continuously converted into electric signals. That is, the range of observation at one time is made an area of, for example, $50\mu \times 100\mu$, and the ranges are repeatedly scanned, whereby a continuous electric signal corresponding to the entire surface of the semiconductor wafer can be obtained. The range which can be observed at one time can be adjusted by changing the size of the aperture of the aperture plate 14 in FIG. 1. Of course, it can also be adjusted by changing the magnifying powers of the lenses (9, 10, 13) of the optical system.

Figure 6:
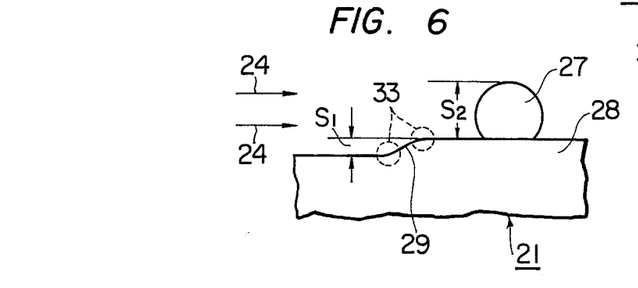
FIG. 6 is a view for explaining the relationship between a normal protuberance and a protuberance of a foreign matter in a semiconductor wafer to-be-inspected.

In the above description of the embodiment, there has been referred to the case where the walls 29 of the bumps 28 of the semiconductor wafer to-be-inspected as conform with the normal pattern are inclined in the specified direction relative to the direction of projection of the light. However, even in case where the wall 29 has another direction at both terminal parts 33 thereof as illustrated in FIG. 6, only the pattern area corresponding to the foreign matter 27 can be observed through the rotational adjustment of the polarizer plate 8 as long as the area $S_1$ in which the bump 28 receives the light 24 is smaller than the area $S_2$ in which the foreign matter 27 receives the light 24.

In the case where this invention is not applied, the light reflected from the etched face is also sensed, and hence, the inspection on the foreign matter is difficult. In contrast, when the method of inspection according to this invention as set forth above is actually applied to the inspection on the foreign matter of a semiconductor wafer, the light reflected from the etched face is not sensed, and only the light irregularly reflected from the foreign matter is sensed, so that the foreign matters can be readily detected on the basis of the result of the sensing.

In particular, according to this invention, the light reflected on the basis of the normal pattern formed of an interconnection layer, a protective layer etc. disposed in the semiconductor wafer is cut by the polarizer plate, so that the discrimination of the normal pattern from the foreign matter pattern can be done without degrading the light sensitivity. In consequence, the signal-to-noise ratio at the time when the pattern of the foreign matter has been converted into the electric signal can be enhanced. In the case where it is intended to detect only the foreign matter pattern areas 27' as in the pattern of FIG. 4c without using the polarizer plate, light sensitivity of the whole system is lowered in conformity with the light sensitivity of the detection pattern of the foreign matters lest the normal pattern areas 29' should be detected. However, the detection signal of the foreign matter pattern becomes feeble, and when the foreign matter pattern areas are small, they cannot be detected.

Figure 7:
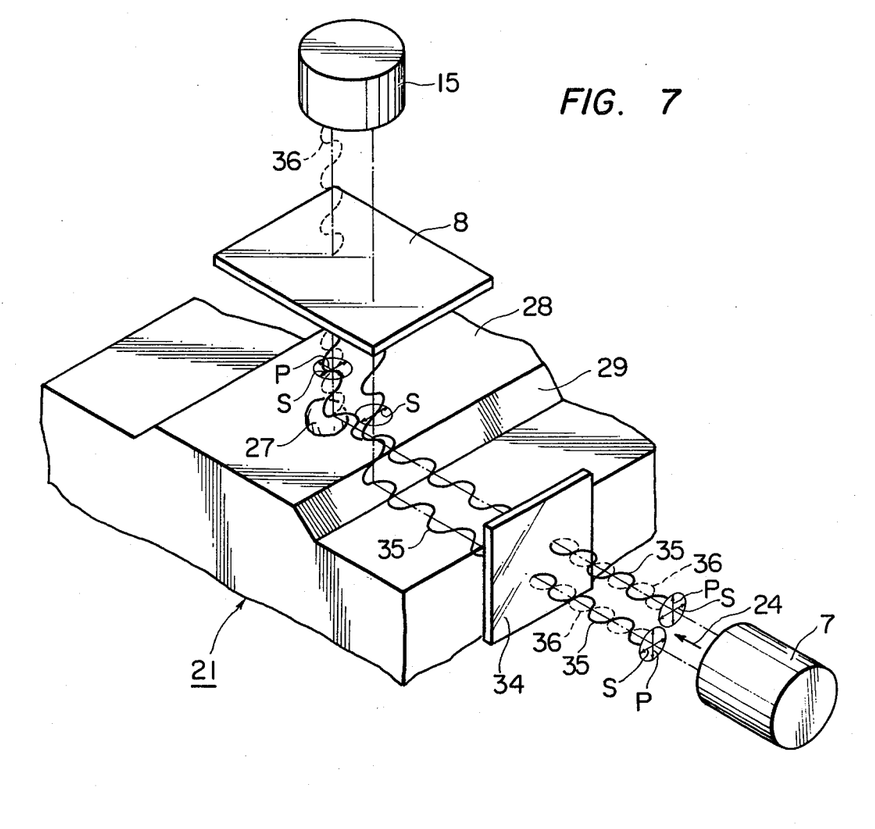
FIG. 7 is an enlarged schematic view showing the essential portions of foreign matter detection apparatus according to another embodiment of this invention.

FIG. 7 is an enlarged view of essential portions showing another embodiment of this invention. Although, in order to readily understand the subject matter of this invention, the lenses 9, 10 and 13 as well as the aperture plate 14 and other parts shown in FIG. 1 are omitted from the illustration, they are installed in the same manner as in FIG. 1.

In this embodiment, a second polarizer plate 34 is added to the end of improving the signal-to-noise ratio of the reflected light from the foreign matter 27. The light source 7 specifically emits the laser beam 24. The polarizer plate 34 is one adapted to pass that light wave (horizontal wave) 35 of the laser light which oscillates in the direction of an s-axis, and to block the light wave (vertical wave) 36 which oscillates in the direction of a p-axis. This polarizer plate is especially installed between the laser source 7 and the semiconductor wafer to-be-inspected 21. Contrariwise to the polarizer plate 34, the polarizer plate 8 which receives the reflected light from the semiconductor wafer acts to block the horizontal wave 35 oscillating in the s-axial direction and to pass the vertical wave 36 oscillating in the p-axial direction.

With such apparatus, the reflected light from the wall 29 of the bump 28 of the semiconductor wafer to-be-inspected comes to have the light wave in the specified direction, so that the unnecessary light wave can be intercepted by the polarizer plate 8 more perfectly.

On the other hand, the foreign matter 27 generates the light wave in the s-axial direction and the light wave in the p-axial direction owing to the irregular reflection based on the rough surface areas thereof, so that only the light wave 36 in the p-axial direction generated from the foreign matter 27 can be received by means of the photoelectric transducer 15 by intercepting the s-axial light wave 35 by means of the polarizer plate 8.

Accordingly, the signal-to-noise ratio which is determined on the basis of the reflected light from the foreign matter pattern and the reflected light from the normal pattern of the semiconductor wafer to-be-inspected 21 can be enhanced, whereby more minute foreign matter can be detected. By way of example, by adopting this system, it has become possible to detect foreign matter which has sizes of several $\mu$.

Figure 8:
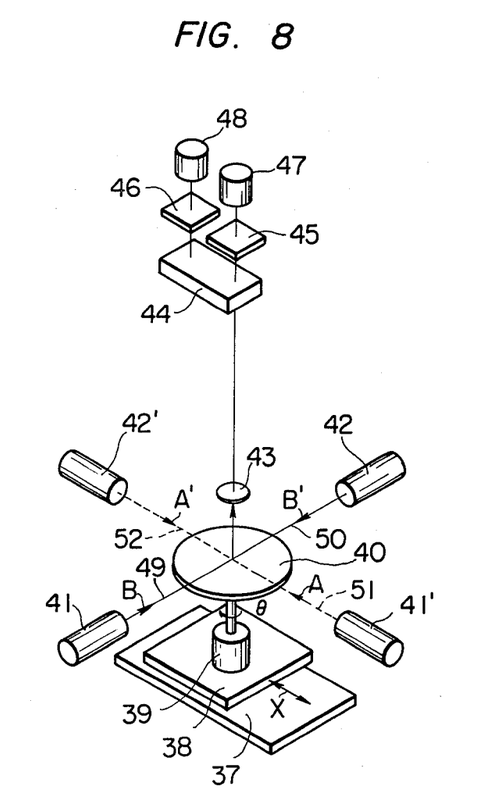
FIG. 8 is a perspective view showing foreign matter detection apparatus according to still another embodiment of this invention.

FIG. 8 shows foreign matter detection apparatus according to still another embodiment of this invention.

In the figure, numerals 37 and 38 designate transfer tables for moving a rest (not shown) of an object to-be-inspected in the direction of X. Numeral 39 indicates a drive portion for endowing the rest with a rotation in the direction of $\theta$. Shown at 40 is the semiconductor wafer to-be-inspected placed on the rest. Numerals 41, 41', 42 and 42' represent laser beam generators. Numeral 43 represents an objective. An optical path separator 44 is made of a polarizer plate. Polarizer plates 45 and 46 serve to intercept specified light waves, respectively. Parts 47 and 48 are photoelectric transducers.

In this apparatus, the two laser light generators 41 and 42 are especially used to facilitate the detection of foreign matter which has a reflective face approximate to the right angle.

Light paths in the apparatus will be explained with reference to FIGS. 9 and 10. In an enlarged view of essential portions in FIG. 9, a semiconductor wafer to-be-inspected 40 is assumed to have a bump 53 of glass (designed beforehand) and unfavorable foreign matter 54 of the same material as that of the bump 53. Using the laser generators, light waves (horizontal waves) 49 and 50 which oscillate in a direction s are projected onto the foreign matter 54 in a direction B-B'. Owing to the light waves, reflected lights 55 and 56 are produced from the foreign matter 54. The reflected lights 55 and 56 come to include also light wave (vertical wave) components oscillating in a p direction on account of the irregular reflection from the foreign matter 54. As illustrated in FIG. 10, when these reflected lights are introduced into the optical path separator 44, the vertical waves 59 and 60 are rectilinearly propagated and are introduced into the photoelectric transducer 47 through the polarizer plate 45. On the other hand, the horizontal waves 61 and 62 of the reflected lights 55 and 56 are bypassed by the optical path separator 44 and are not introduced into the photoelectric transducer 47. That is, the horizontal wave components generated from the laser generators 41 and 42 are not introduced into the photoelectric transducer 47, and the photoelectric transducer 47 receives only the vertical wave components from the foreign matter. Accordingly, the presence of the foreign matter 54 can be detected by distinguishing the reflected light of the foreign matter from that of the wall of the bump 53 conforming with the normal pattern.

Referring to FIG. 9 again, in order to examine the pattern of the foreign matter 54 more precisely, the foreign matter 54 may be inspected also in a direction A-A' orthogonal to the direction B-B'. This can be carried out similarly to the above. The laser generators 41' and 42' introduce horizontal light waves 51 and 52 oscillating in the s direction into the foreign matter 54, respectively. As seen from FIG. 10, reflected lights 57 and 58 respectively based on the projection of the horizontal light waves 51 and 52 into the foreign matter 54 include horizontal light wave components and vertical light wave components likewise to the reflected lights 55 and 56.

Figure 9:
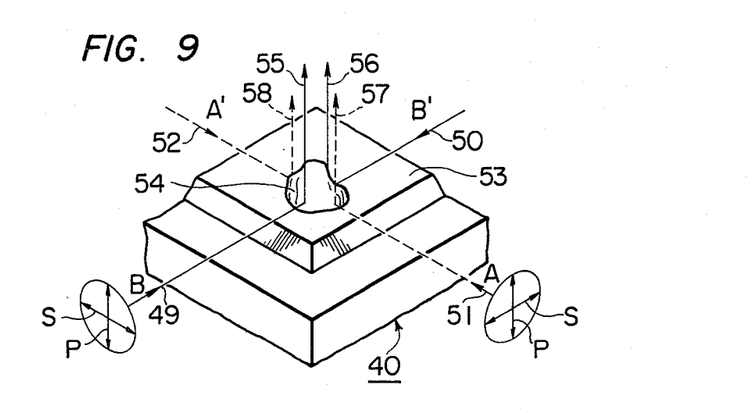
FIG. 9 is a view illustrative of the relationship between a semiconductor wafer and projected light for explaining the operation of the foreign matter detection apparatus of this invention shown in FIG. 8.
Figure 10:
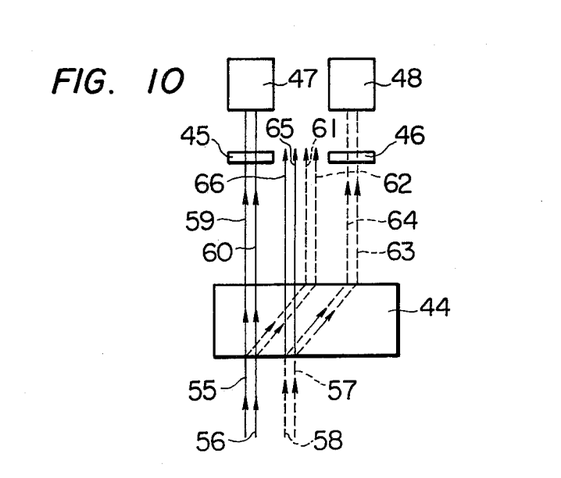
FIG. 10 is a view illustrative of the state of introduction of reflected light into an optical path separator for explaining the operation of the foreign matter detection apparatus of this invention shown in FIG. 8.

In this case, the horizontal wave components of the reflected lights from the foreign matter 54 are the light waves oscillating in the B-B' direction indicated in FIG. 9, and they oscillate in the direction orthogonal to the horizontal wave components of the reflected lights oscillating in the A-A' direction as based on the lights directed from the laser generators 41 and 52 towards the foreign matter 54. On the other hand, the vertical wave components reflected from the foreign matter 54 are the light waves oscillating in the A-A' direction indicated in FIG. 9, and they oscillate in the direction orthogonal to the vertical components (oscillating in the B-B' direction) generated in such a manner that the lights from the laser generators 41 and 42 are reflected by the foreign matter 54. The reason therefor is that the laser generators 41' and 42' lie at the positions geometrically shifting 90° relative to the laser generators 41 and 42.

Accordingly, when the reflected lights 57 and 58 from the foreign matter 54 are introduced into the optical path separator 44, horizontal waves 65 and 66 are rectilinearly propagated and are not introduced into the photoelectric transducer 48 as illustrated in FIG. 10. On the other hand, vertical waves 63 and 64 have the paths altered and are introduced into the polarizer plate 46 adapted to pass only the vertical waves corresponding to the light sources 41' and 42'. The vertical waves 63 and 64 having passed through the polarizer plate 46 are introduced into the photoelectric transducer 48, and are converted into electric signals. In this way, only the vertical waves generated from the foreign matter 54 are sensed, and the foreign matter pattern is recognized.

In accordance with this embodiment, the foreign matter detection in the four directions can be simply performed by the use of the optical path separator 44 constructed of the polarizer plate. Although the embodiment has been explained as employing the four laser generators, the inspection in the four directions is also possible by employing one or two laser generators and moving it or them sequentially.

In the case where, in the foregoing embodiment, the vertical waves oscillating in the p direction are used as the laser beams to be emitted from the laser generators 41' and 42' in the A-A' direction, the horizontal wave components (oscillating in the B-B' direction in FIG. 9) of the reflected lights to appear from the foreign matter 54 on the basis of the laser beams are light waves which oscillate in the same direction as that of the vertical wave components (oscillating in the B-B' direction in FIG. 9) of the reflected lights from the foreign matter 54 as based on the laser beams (horizontal waves) of the laser generators 41 and 42. Therefore, the foreign matter detection can be executed with only the pair of the polarizer plate 45 and the photoelectric transducer 47 by omitting the optical path separator 44, the polarizer plate 46 and the photoelectric transducer 48.

Likewise to the case illustrated in FIG. 5, the inspection can be conducted over the whole semiconductor wafer surface continuously and concentrically at a certain stipulated pitch through the medium of the transfer tables 37 and 38 and the drive portion 39.

As thus far described, according to this invention, only the reflected light from the foreign matter can be sensed, so that even when the protuberances in the protective film, interconnection layer etc. formed in the surface of the semiconductor wafer exist, only the foreign matter can be distinguished from them and detected, resulting in the betterment of the signal-to-noise ratio.

In addition, according to this invention, the pattern of the foreign matter can be continuously converted into the electric signal, so that an automated inspection on the foreign matter is made possible by introducing electronic circuitry such as computer. It is also possible to easily prepare data for the analysis of defects such as causes for the occurrence of the foreign matter.

Although the embodiments of this invention have been described as to the case where the foreign matter is of the glass substance, this invention is also applicable to the detection of unfavorable foreign matters which appear during the formation of a silicon nitride ($Si_3N_4$) film, a polycrystalline silicon interconnection film, a passivation film of any material other than phosphosilicated glass previously referred to, etc. for a semiconductor wafer and which are made of substances identical to or different from those of the films. Further, this invention is applicable, not only to the foreign matter inspection of the semiconductor wafer, but also to the inspection of a photo-mask.

This invention can be subject to various modifications within a scope not departing from the spirit thereof.

What is claimed is:

1. Inspection apparatus for detecting foreign matter existent on a surface of an object, comprising:
   light emission means for projecting light towards the object to-be-inspected sidewards of said object;
   first polarization means for polarizing light reflected from the surface of said object to-be-inspected;
   detection means for detecting the reflected light obtained after the passage through said polarization means; and
   wherein said light emission means includes means for projecting light from at least two different sides of said object to-be-inspected.

2. Inspection apparatus for detecting the existence of a protuberance projecting on the surface of an object, comprising:

a rest for placing the object to-be-inspected;

light emission means for directing an incident light beam toward the surface of said object placed on said rest in a direction substantially parallel to the surface of said object;

polarization means for polarizing a light beam which is reflected in a direction substantially perpendicular to the surface of said object from the surface of said object; and detecting means for detecting the intensity of the light passing through said polarization means with respect to said reflected beam from the surface of said object, wherein said light emission means comprises means for directing at least two incident light beams toward the surface of said object placed on said rest in directions substantially parallel to the surface of said object, said two incident light beams being respectively directed in different directions extending from at least two different sides of said object to an area of the surface of said object.

3. Inspection apparatus according to claim 2, wherein said detecting means comprises means for detecting the intensity of the two light beams passing through said polarization means in relation with said two incident light beams.

4. Inspection apparatus according to claim 3, further comprising an optical path separator for separating said two light beams passing through said polarization means so as to direct the passing of said two light beams in different directions.

5. Inspection apparatus according to any one of claims 2-4, further comprising driving means for rotating said rest.

6. Inspection apparatus for detecting the existence of a protuberance projecting on the surface of an object, comprising:

a rest for placing the object to-be-inspected;

light emission means for directing an incident light beam toward the surface of said object placed on said rest in a direction substantially parallel to the surface of said object;

polarization means for polarizing a light beam which is reflected in a direction substantially perpendicular to the surface of said object from the surface of said object;

detecting means for detecting the intensity of the light passing through said polarization means with respect to said reflected beam from the surface of said object, further comprising driving means for rotating said rest.

* * * * *